United States Patent
Schlangen et al.

(10) Patent No.: US 11,252,943 B2
(45) Date of Patent: Feb. 22, 2022

(54) ILLUMINATING AN ENVIRONMENT

(71) Applicant: SIGNIFY HOLDING B.V., Eindhoven (NL)

(72) Inventors: Lucas Josef Maria Schlangen, Eindhoven (NL); Rémy Cyrille Broersma, Eindhoven (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 0 days.

(21) Appl. No.: 16/761,977

(22) PCT Filed: Nov. 6, 2018

(86) PCT No.: PCT/EP2018/080236
§ 371 (c)(1),
(2) Date: May 6, 2020

(87) PCT Pub. No.: WO2019/086688
PCT Pub. Date: May 9, 2019

(65) Prior Publication Data
US 2021/0195718 A1    Jun. 24, 2021

(30) Foreign Application Priority Data
Nov. 6, 2017   (EP) ..................................... 17200041

(51) Int. Cl.
*A01K 45/00*    (2006.01)
*H05B 45/20*    (2020.01)
*H05B 47/155*    (2020.01)
*H05B 47/16*    (2020.01)
(Continued)

(52) U.S. Cl.
CPC .............. *A01K 45/00* (2013.01); *H05B 45/20* (2020.01); *H05B 47/155* (2020.01); *H05B 47/16* (2020.01); *H05B 47/165* (2020.01); *H05B 47/17* (2020.01)

(58) Field of Classification Search
CPC ...... H05B 47/16; H05B 47/17; H05B 47/165; A01K 45/00; A01K 31/22; A01K 1/00
See application file for complete search history.

(56) References Cited

U.S. PATENT DOCUMENTS 8,884,527 B2   11/2014   Lin et al.
8,941,306 B2   1/2015   Ayres
(Continued)

FOREIGN PATENT DOCUMENTS

WO    201506070 A1    1/2015

*Primary Examiner* — Daniel D Chang (57) ABSTRACT

A method of emitting light from one or more light emitting elements, the method comprising: emitting a first time period of photopic light, followed by emitting a first time period of scotopic light, followed by emitting a second time period of photopic light, and followed by emitting a second time period of scotopic light; wherein a first transition from the first time period of photopic light to the first time period of scotopic light is different compared to a second transition from the second time period of photopic light to the second time period of scotopic light, and/or wherein a third transition from the first time period of scotopic light to the second time period of photopic light is different compared to a fourth transition from the second time period of scotopic light to the first time period of photopic light or a third time period of photopic light.

17 Claims, 4 Drawing Sheets

(51) Int. Cl.
*H05B 47/17* (2020.01)
*H05B 47/165* (2020.01)

(56) References Cited

U.S. PATENT DOCUMENTS

| | | | |
|---|---|---|---|
| 2012/0038284 A1* | 2/2012 | Setomoto | H05B 45/46 |
| | | | 315/192 |
| 2016/0366746 A1* | 12/2016 | van de Ven | F21V 29/74 |
| 2017/0290124 A1* | 10/2017 | Grajcar | H05B 45/20 |

* cited by examiner

ILLUMINATING AN ENVIRONMENT

CROSS-REFERENCE TO PRIOR APPLICATIONS

This application is the U.S. National Phase application under 35 U.S.C. § 371 of International Application No. PCT/EP2018/080236, filed on Nov. 6, 2018, which claims the benefit of European Patent Application No. 17200041.6, filed on Nov. 6, 2017. These applications are hereby incorporated by reference herein.

TECHNICAL FIELD

The present disclosure relates to a method of emitting periods of photopic and scotopic light from light emitting elements.

BACKGROUND

In a chicken farm, broiler chickens (chickens bred and raised specifically for meat production) grow optimally when reared under a light-dark cycle that has a period of approximately twenty four hours and consists of multiple scotopic and photopic periods of light per twenty four-hour cycle. Scotopic light is low level light, with scotopic vision referring to vision of the eye under low light conditions. Photopic light is well-lit light, with photopic vision referring to vision of the eye under well-lit conditions. The chicken only experiences one scotopic period of light (usually the longest) as the subjective night. A gradual transition between light and darkness is less stressful for the chickens as it helps the chickens settle down for the night in a more gradual and orderly fashion. In addition, it helps the chickens to increase food intake before the subjective night. An increased crepuscular feeding activity ensures the chickens have a full crop (the thin-walled expanded portion of the alimentary tract used for the storage of food prior to digestion) at the beginning of the night.

US 2017/0290124 A1 discloses a control system for illuminating swine having one or more controllers configured to increase voltage supplied to a first plurality of lights to a first threshold voltage to illuminate the first plurality of lights to provide a first light having a first color characteristic that affects swine. In embodiments, the first light is red light which is not perceived by the swine and hence simulates night conditions. The one or more controllers are also configured to increase the voltage supplied to a second plurality of lights to a second threshold voltage to illuminate the second plurality of lights to provide a second light with a second color characteristic different than the first color characteristic. In embodiments, the second light is white light. The one or more controllers are also configured to increase the voltage supplied to a third plurality of lights to a third threshold voltage to illuminate the third plurality of lights to provide third light with a third color characteristic that stimulates the swine to have a predetermined behavior. In embodiments, the third light is blue light which stimulates the swine to eat.

SUMMARY

According to a first aspect disclosed herein, there is provided a method of emitting light from one or more light emitting elements each controllable to emit respective light, the method comprising: emitting a first time period of photopic light, followed by emitting a first time period of scotopic light, followed by emitting a second time period of photopic light, and followed by emitting a second time period of scotopic light; wherein a first transition from the first time period of photopic light to the first time period of scotopic light is different compared to a second transition from the second time period of photopic light to the second time period of scotopic light, and/or wherein a third transition from the first time period of scotopic light to the second time period of photopic light is different compared to a fourth transition from the second time period of scotopic light to the first time period of photopic light or a third time period of photopic light.

That is, a sequence of alternating photopic and scotopic light is emitted with a different transition from one period of photopic light to an immediately following respective period of scotopic light compared to a transition from another period of photopic light to its immediately following respective period of scotopic light. Additionally or alternatively, there is a different transition from one period of scotopic light to an immediately following respective period of photopic light compared to a transition from another period of scotopic light to its immediately following respective period of photopic light.

Typical lighting installations only use one type of light to dark (dawn to dusk) or dark to light (dusk to dawn) transition for all scotopic periods. This means that the chicken cannot reliably conclude from the light to dark transition alone which scotopic period is the subjective night. The method of disclosed herein is advantageous as it provides a different light to dark (dawn to dusk) or dark to light transition for a particular period of scotopic light (the subjective night). That is, the chickens can conclude from the different transition that the upcoming scotopic period is the subjective night.

Whilst examples described herein are applicable to illuminating an environment occupied by chickens, the examples are equally applicable to illuminating an environment occupied by other animals or living beings. In particular, the examples are also applicable to illuminating an environment occupied by humans and especially infants. For example, infants benefit from knowing when the onset of the subjective night is about to occur. This can be achieved by the different transition for the longest period of scotopic light.

Additionally, transitioning from the subjective night to photopic light in a different manner compared to transitioning from a shorter period of scotopic light to photopic light further helps the chickens or other such beings to understand that the subjective night has finished. In examples, the fourth transition may occur over a longer time period than the third transition. In additional or alternative examples, the fourth transition comprises light of a different intensity and/or spectral profile compared to the third transition.

In examples, the first transition occurs over a first transition time period and the second transition occurs over a second, different transition time period and/or the third transition occurs over a third transition time period and the fourth transition occurs over a fourth, different transition time period.

In examples, the second transition time period is greater than the first transition time period and/or the fourth transition time period is greater than the third transition time period.

This is advantageous as the transition from photopic light to the subjective night (e.g. the longest period of scotopic light) is more gradual and therefore is less stressful for the chickens or other beings.

In examples, the third transition comprises light of a third intensity profile and the fourth transition comprises light of a fourth, different intensity profile.

In examples, the first transition comprises light of a first spectral profile and the second transition comprises light of a second, different spectral profile.

Transitioning from scotopic light to the subjective night uses light of a different spectral and/or intensity profile helps to provide a clear signal to the chickens or other beings of the arrival of the subjective night.

In examples, the third transition comprises light of a third spectral profile and the fourth transition comprises light of a fourth, different spectral profile.

In examples, the method comprises repeating a light cycle, wherein the repeated light cycle comprises consecutive periods of photopic and scotopic light comprising at least the first and second time periods of photopic light and the first and second time periods of scotopic light.

In examples, the second time period of scotopic light is emitted once per light cycle.

In examples, the light cycle is emitted over a time period of one day.

That is, the first and second periods of photopic and scotopic light form part of a light cycle that is repeated, for example, over a period of one day (approximately twenty four hours). In examples, the light cycle may additionally comprise the third period of photopic light.

Repeating the light cycle provides a memorable rhythm of light for the chickens or other beings. Advantageously, emitting the second period of scotopic light (the subjective night) only once per light cycle, further helps the chickens or other beings to understand that said fourth period is the subjective night.

In examples, the second transition from photopic light to scotopic light is different compared to all other transitions between photopic light and scotopic light.

In examples, the second time period of scotopic light is greater than the first time period of scotopic light and/or the first and second time periods of photopic light.

That is, in some examples the subjective night is longer than any of the period of "daytime" light.

In examples, the time periods are programmable by an end-user.

Advantageously, the time periods can be user-defined and updated, e.g. via a central control system or remote control. For example, the subjective night may be increased during the winter months to reflect the change in real-world night duration. As an example, the subjective night may be increased around the winter solstice.

In examples, the photopic light and scotopic light respectively correspond to human photopic vision and scotopic vision ranges.

That is, the photopic and scotopic light may be advantageously set to correspond to an average human's photopic and scotopic light respectively, mimicking real-world light conditions. In examples, the photopic light and scotopic light respectively correspond to an average (newborn) baby's or infant's vision. The inventors have recognised that the method described herein may also be useful for babies in neonatal intensive care units, for example, to help new-born children to sleep (or fall asleep) more easily. In examples, the photopic and scotopic light may respectively correspond to an average elderly (e.g. a sufferer of dementia) human's photopic and scotopic vision.

In examples, the photopic light and scotopic light respectively correspond to chicken photopic vision and scotopic vision ranges.

That is, the photopic and scotopic light may be advantageously set to correspond to the chicken's photopic and scotopic light respectively, mimicking real-world light conditions. This helps to provide a natural environment for the chickens. In examples, the photopic and scotopic light respectively correspond to an animals photopic and scotopic vision, e.g. a sheep, cow, pig.

In examples, the light emitted from the one or more light emitting devices is optical light.

In examples, the light emitted from the one or more light emitting devices may be infrared light or ultraviolet light.

According to a second aspect disclosed herein, there is provided a lighting system comprising one or more light emitting elements each controllable to emit respective light and configured to: emit a first time period of photopic light, followed by emitting a first time period of scotopic light, followed by emitting a second time period of photopic light, and followed by emitting a second time period of scotopic light; wherein a first transition from the first time period of photopic light to the first time period of scotopic light is different compared to a second transition from the second time period of photopic light to the second time period of scotopic light, and/or wherein a third transition from the first time period of scotopic light to the second time period of photopic light is different compared to a fourth transition from the second time period of scotopic light to the first time period of photopic light or a third time period of photopic light.

According to a third aspect disclosed herein, there is provided a computer program product comprising code embodied on computer-readable storage and configured so as when run on one or more processing units of a control system to control one or more light emitting elements to perform operations in accordance with any of the method steps disclosed herein.

BRIEF DESCRIPTION OF THE DRAWINGS

To assist understanding of the present disclosure and to show how embodiments may be put into effect, reference is made by way of example to the accompanying drawings in which.

DETAILED DESCRIPTION

Typical lighting systems only use one kind of dawn/dusk (dawn and/or dusk) transition for all scotopic periods. Due to the transitions being the same kind, the chicken cannot conclude from the dawn/dusk transition alone which scotopic period is the subjective night. This can be stressful for the chickens and prevent optimal growth.

The invention disclosed herein relates to a lighting device or system which can implement an approximate 24 hours light-dark cycle that uses different dawn/dusk transitions for the long and short dark periods. The dawn/dusk transitions can differ in duration (e.g. 5 minutes for a 1 hour scotopic period and 30 minutes for a four hour scotopic period, i.e. the subjective night) and/or their dynamics (e.g. intensity, spectrum, etc.).

The invention gives a less stressful transition period and gives a clearer signal to the chickens on the arrival of the subjective night (or the departure from the subjective night) as opposed to the standard scotopic periods during the day.

The invention is not only beneficial for chicken farming but can also be used in hospitals, e.g. in neonatal intensive care units.

Figure 1:
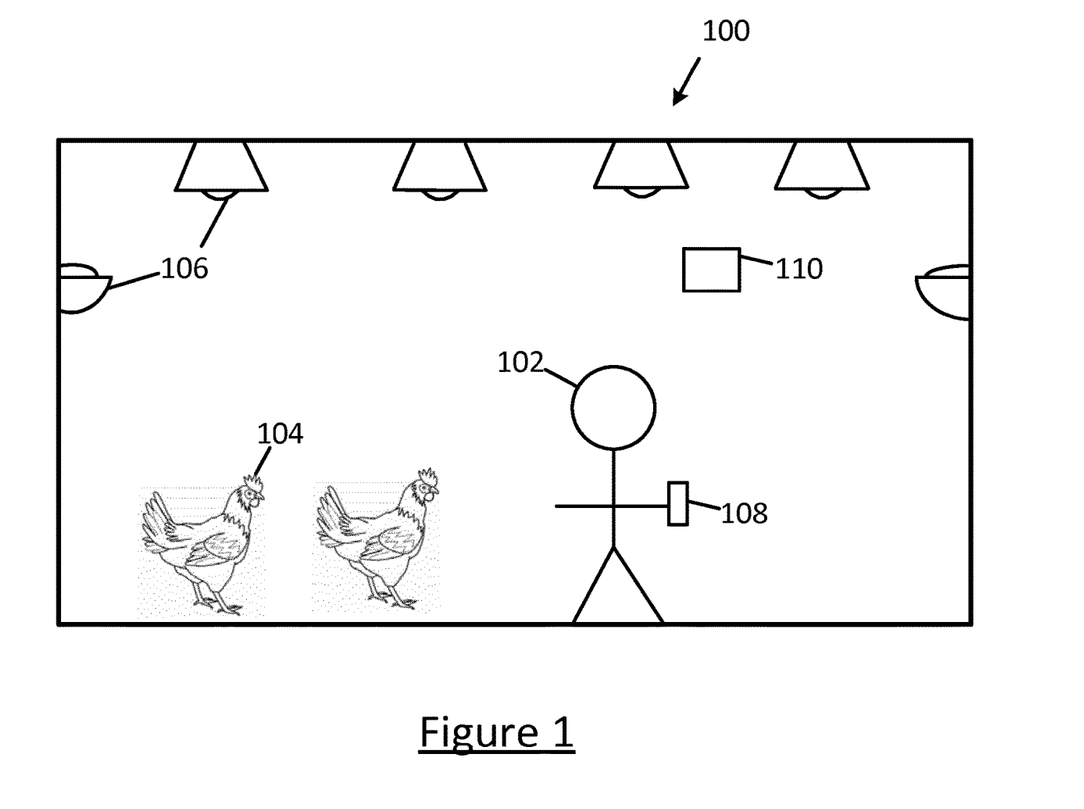
FIG. 1 shows schematically an environment comprising a lighting system for illuminating the environment.

FIG. 1 illustrates an example environment 100 in which embodiments disclosed herein may be employed. The environment 100 is a space that may be occupied by one or more users 102 and/or one or more animals, such as chickens 104. The environment 100 may take the form of an indoor space such as one or more rooms of a home, office or other building such as a barn or farmhouse; an outdoor space such as a garden or park; a partially covered space such as a gazebo; or a combination of such spaces such as a farm comprising both indoor and outdoor spaces.

The environment 100 is equipped with a plurality of light emitting elements (or light sources or luminaires) 106 installed or otherwise disposed at different locations throughout the environment 100. A light emitting element 106 may refer to any kind of light emitting device for illuminating an environment or part of the environment occupied by a user 102 or animal 104, whether providing ambient lighting or task lighting. Each of the light emitting elements 106 may take any of a variety of possible forms, such as a ceiling or wall mounted luminaire, a free-standing floor or table light source 106, an light source 106 mounted on a pole, gantry or rigging; or a less traditional form such as an light source 106 embedded in a surface or item of furniture (and the different light sources 106 in the environment 100 need not take the same form as one another). Alternatively, the light emitting element may take the form of head mounted glasses or light emitting contact glasses. Whatever form it takes, each light emitting element 106 comprises at least one lamp (light element) and any associated housing, socket and/or support. Examples of suitable lamps include LED-based lamps, or traditional filament bulbs or gas discharge lamps.

In some scenarios the environment 100 may be divided into a plurality of different zones or localities (not shown), such as different rooms, each illuminated by a different respective subset of one or more of the light emitting elements 106. For example, the different zones may relate to different sections of a farmhouse or chicken coup. In another example, the different zones may relate to different rooms or sections of a hospital.

The environment 100 may also be equipped with one or more lighting control devices 108. Each of the lighting control devices 108 may take the form of a stand-alone lighting control device 108 such as a smart light switch, a dimming switch, etc. or alternatively a lighting control device 108 integrated in another user device such as a mobile user terminal such as a smartphone or tablet, or even a wearable device that can be worn about the user's person. For example, the user terminal may be installed with a suitable lighting control app. The lighting control device 108 can be mains powered, battery powered, or use energy-harvesting techniques to supply its energy. The lighting control device 108 is configured to be able to control the light emitted by one or more light emitting elements 106 in the environment 100. This may include switching the light emitting elements 106 on/off, controlling the colour of the light, controlling the dimming level, controlling a time-varying effect of the light, controlling a spatial-varying effect of the light or adjusting any other aspects of the light that may be applicable to the light emitting elements 106 within the environment 100. The environment 100 may also be equipped with a central lighting bridge 110.

Figure 2:
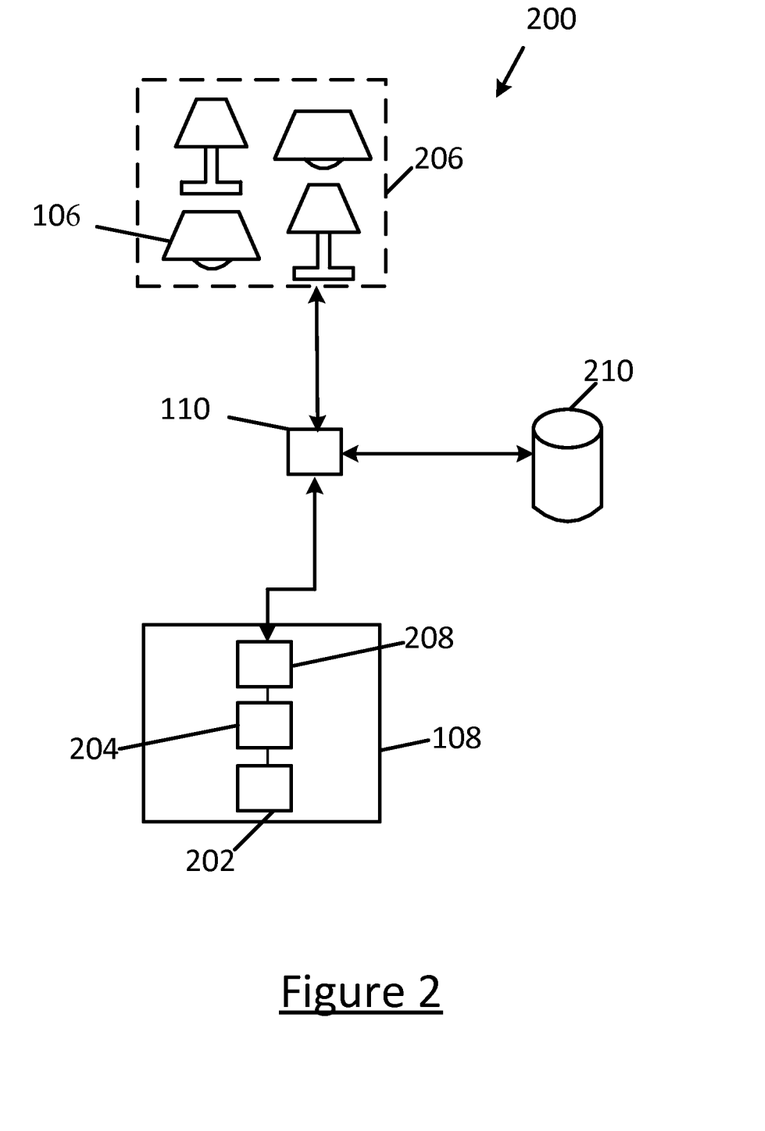
FIG. 2 shows schematically a block diagram of a control system for controlling a lighting system.

FIG. 2 illustrates a control system 200 enabling the user 102 to control the light from one or more of the light emitting elements 106 based on one or more inputs from the user 102 to a lighting control device 108 and/or the light state of the light emitting elements 106. This may be to control the light in the same part of the environment 100 as that in which the user 102 inputs a command to the lighting control device 108 or a different part of the environment 100.

A database 210 is shown in FIG. 2. The database is configured to store one or more settings associated with the one or more light emitting elements 106. For example, the database 210 may store program settings, or settings defining the photopic and scotopic light periods and the transitions between those periods detailed herein. The database 210 may be stored on the lighting control device 108, the central lighting bridge 110, a server or on one or more light emitting elements 106.

The lighting control device 108 comprises a user interface 202 arranged to receive an input from the user 102 and operatively coupled to a controller 204. The user interface 202 may comprise a display in the form of a screen and means for receiving inputs from the user. For example, the user interface 202 may comprise a touch screen, or a point-and-click user interface comprising a mouse, track pad, or tracker ball or the like. Alternatively or in addition, the user interface 202 may comprise a dedicated lighting control unit comprising a dedicated actuator or control panel for controlling the light emitting elements 106 within the environment 100. For example, the lighting control device 108 may be in the form of a dedicated control unit (wired or wireless) which can be manually operated by the user 102, e.g. by using one or more buttons, sliders, switches and/or dials of the dedicated control unit.

Alternatively or additionally, the user interface 202 may comprise a microphone for receiving a voice command from the user. In another example, the user interface 202 may comprise a camera, infrared detector or the like for detecting gesture commands from the user.

The lighting control device 108 comprises the controller 204 coupled to the user interface 202 in order to receive an indication of the user's commands. The controller 204 is also operatively coupled to a lighting system 206 comprising the one or more light emitting elements 106 discussed in relation to FIG. 1 via a wireless transceiver 208. The controller 204 can thereby control the lighting system 206 based on the identified commands in order to select a particular program. For example, the user 102 may select between programs of different time scales, e.g. a first program may emit the periods of photopic and scotopic light according to the present invention over a time period of twenty four hours, whilst a second program may emit the periods of light over a time period of twelve hours. The controller 204 is configured to retrieve the one or more settings from the database 210, e.g. in response to an input to the user interface 202.

In embodiments the controller 204 is implemented in the form of software stored in memory and arranged for execution on a processor (the memory on which the software is stored comprising one or more memory units employing one or more storage media, e.g. EEPROM or a magnetic drive, and the processor on which the software is run comprising one or more processing units). Alternatively it is not excluded that some or all of the controller 204 could be implemented in dedicated hardware circuitry, or configurable or reconfigurable hardware circuitry such as a PGA or FPGA. Whatever form it takes, in embodiments the controller 204 may be implemented internally in a single lighting control device 108 along with the user interface 202 and a wireless transceiver 208, i.e. in the same housing. Alternatively the controller 204 could, partially or wholly, be implemented externally such as on a central lighting bridge 110 or server comprising one or more server units at one or more geographic sites (not shown).

The controller 204 may be configured to perform some or all of the actions of the lighting control device 108 disclosed herein. For example, the controller 204 is configured to receive the user commands via the user interface 202. The controller 204 is also configured to communicate with one or more light emitting elements 106 within the environment 100 via the wireless transceiver 208 and/or where applicable, the controller 204 is also configured to communicate with the central lighting bridge 110 or server via the wireless transceiver 208.

The lighting control device 108 comprises the wireless transceiver 208 for communicating via any suitable wireless medium, e.g. a radio transceiver for communicating via a radio channel (though other forms are not excluded, e.g. an ultrasound or infrared transceiver). The wireless transceiver 208 may comprises a Wi-Fi, ZigBee, Bluetooth, Thread etc. interface for communicating with the light emitting elements 106. Each light emitting element 106 is configured to be able to communicate over a wireless channel in order to perform the respective control operations disclosed herein, preferably a radio channel (though the possibility of other media such as visual light communications, ultrasound or infrared are not excluded). For instance the radio channel may be based on a radio access technology such as ZigBee, Bluetooth, Wi-Fi, Thread, JupiterMesh, Wi-SUN, 6LoWPAN, etc. The radio channel can be used by the lighting control device 108 to control the light emitting elements 106.

It is also not excluded that a wired connection could alternately, or additionally, be provided between the central device 108 and the light emitting elements 106 for control purposes, e.g. an Ethernet or DMX connection.

Alternatively, the wireless transceiver 208 may communicate with the light emitting elements 106 via the central lighting bridge 110 or a server, for example, over a local area network or a wide area network such as the internet. In the case of receiving commands direct from the lighting control device 108, the light emitting elements 106 each comprise a respective wireless receiver or transceiver (not shown) for connecting directly to the control device 108. Alternatively, the light emitting elements 106 may each comprise a wired or wireless connection to communicate with the central lighting bridge 110 or a server. The light emitting elements 106 may also receive the control commands via the central lighting bridge 110 or server via a wireless connection.

In embodiments the functionality of the central lighting bridge 110 or server is implemented in the form of software stored in memory and arranged for execution on a processor (the memory on which the software is stored comprising one or more memory units employing one or more storage media, e.g. EEPROM or a magnetic drive, and the processor on which the software is run comprising one or more processing units). Alternatively it is not excluded that some or all of the functionality of the central lighting bridge 110 or server could be implemented in dedicated hardware circuitry, or configurable or reconfigurable hardware circuitry such as a PGA or FPGA. Also note again that the central lighting bridge 110 or server may be implemented locally within the environment 100 or at a remote location, and may comprise one or more physical units at one or more geographic sites.

The central lighting bridge 110 may comprise a wireless transceiver. The wireless transceiver may comprise a Wi-Fi, ZigBee, Bluetooth, Thread etc. interface for communicating with the light emitting elements 106, lighting control device 108, central lighting bridge 110 or server over a local and/or wide area network. For instance a radio channel may be based on a radio access technology such as ZigBee, Bluetooth, Wi-Fi, Thread, JupiterMesh, Wi-SUN, 6LoWPAN, etc. Alternatively or additionally, in embodiments the central lighting bridge 110 may comprise a wired connection for communicating with the light emitting elements 106, lighting control device 108, central lighting bridge 110 or server.

In examples, instead of being located on the lighting control device 108, the controller 204 may instead be located, in whole or in part, on the central lighting bridge 110 or server.

Whatever implementation in terms of physical infrastructure, the controller 204 on the control device 108, the bridge 110 or the server may be configured to control light emitting elements 106 in accordance with the following.

Figure 3A:
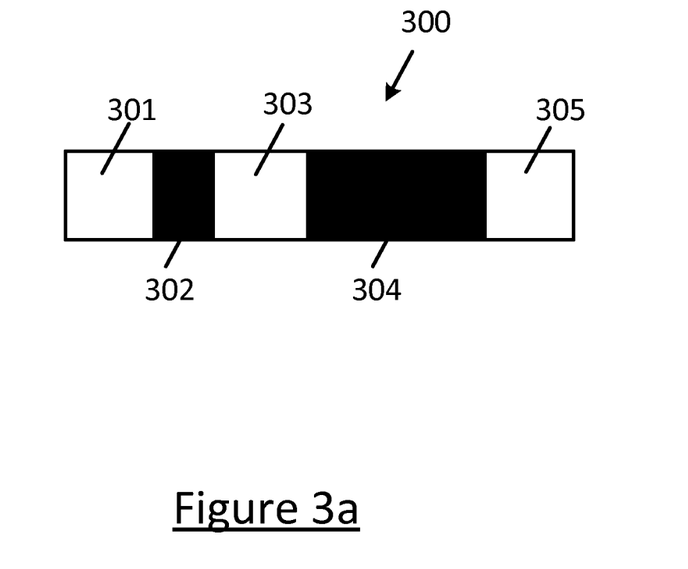
FIG. 3a shows schematically a first example light cycle.

FIG. 3a illustrates a first example light cycle 300. The light cycle 300 comprises multiple photopic periods (shown as white regions) and multiple scotopic periods (shown as black regions). The first example light cycle 300 comprises the first period 301 of photopic light, the first period 302 of scotopic light, the second period of photopic light 303, the second period of photopic light 304 and (optionally) the third period of scotopic light 305. As shown in FIG. 3a, the first light cycle 300 comprises a scotopic period of longer length. This is the subjective night 304.

Figure 3B:
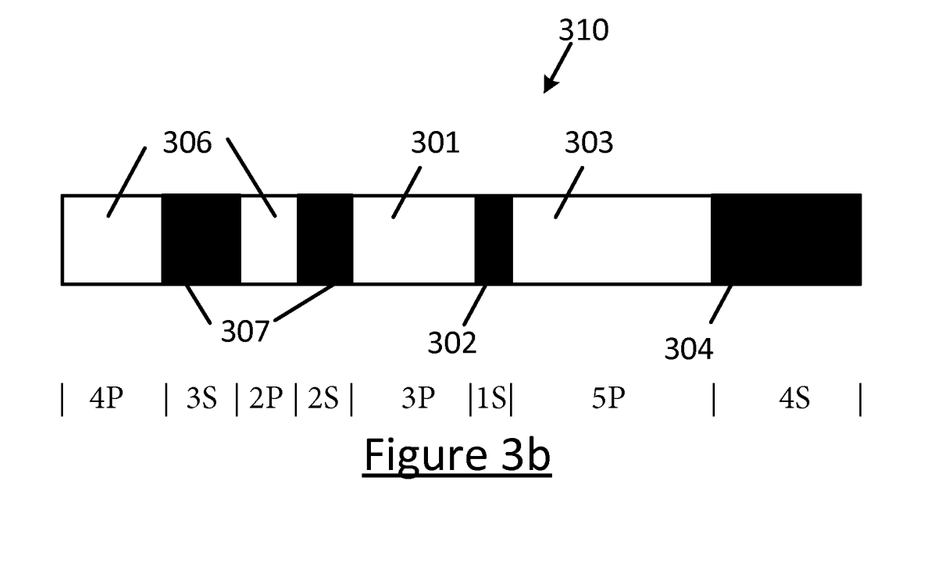
FIG. 3b shows schematically a second example light cycle.

FIG. 3b illustrates a second example light cycle 310. The second example light cycle 310 comprises the first period 301 of photopic light, the first period 302 of scotopic light, the second period of photopic light 303, the second period of scotopic light 304. In addition, the second example light cycle comprises additional periods of photopic light 306 and additional periods of scotopic light 307.

In examples, the environment 100 may be illuminated by one or more light emitting elements 106. The environment 100 may be illuminated by emitting photopic light 301 for a first time period of photopic light, followed by emitting scotopic light 302 for a first time period of scotopic light, followed by emitting photopic light 303 for a second time period of photopic light, and followed by emitting scotopic light 304 for a second time period of scotopic light. The first and second time periods may be equal or different.

In examples, the second time period of scotopic light is greater than the first time period of scotopic light. The second time period may be substantially greater than the first time period such that it is discernibly greater. For example, the second time period may be four hours and the first time period may be one hour. It will be appreciated that the second time period may be greater or less than four hours and the first time period may be greater or less than one hour. The first and second time periods, as mentioned above, may alternatively be equal.

In examples, the second time period of scotopic light may be greater than the first and/or second time periods of photopic light. E.g. the subjective night 304 may be the longest period of continuous (albeit low level) light. In examples, the second time period of scotopic light may be less than the first and/or second time periods of photopic light. For example, a period of photopic light may be the longest period of continuous light (e.g. the subjective day).

Photopic light refers to light that results in photopic vision (the vision of the eye under well-lit conditions or high ambient light levels) and usually allows for colour perception. An example of photopic light is daylight conditions. Photopic vision is typically mediated by cones of the retina. Typically photopic light for humans means light having an illuminance above 30 lx (or a luminance above e.g. 3 cd/m$^2$). Due to differences in the visual system between different animal species, this limit can differ between animals.

Scotopic light refers to light that results in scotopic vision (the vision of the eye under low light conditions or low ambient light levels). An example of scotopic light is night-time conditions. Scotopic vision is typically mediated by rods of the retina. Typically scotopic light for humans means light having an illuminance below a few lux (e.g. 1 lx) or a luminance below e.g. 0.003 cd/m$^2$. Due to differences in the visual system between different animal species, this limit can differ between animals.

In examples, photopic light is different to scotopic light in at least one of the following: brightness, intensity profile, spectral profile. In examples, photopic light results in a lighter environment than scotopic light which results in a darker environment.

In examples, the light emitted during the periods of photopic and/or scotopic light may vary in time and/or space and/or in their characteristics (e.g. intensity). In examples, the light emitted during these periods may be constant.

In examples, the photopic light emitted for the first 301 and second 303 time periods may have the same characteristics (e.g. brightness, colour). Alternatively, the photopic light emitted for these periods may differ.

In examples, the scotopic light emitted for the first 302 and second 304 time periods may have the same characteristics (e.g. brightness, colour). Alternatively, the scotopic light emitted for these periods may differ. For example, the second period of scotopic light 304 may be perceptively darker than the first period of scotopic light 302.

In examples, the first transition from photopic light to scotopic light is different compared to the second transition from photopic light to scotopic light. For example, the transition from photopic light to scotopic light may refer to any state of the light emitted by the one or more light emitting elements 106 in between a period of average photopic light and average scotopic light. In another example, the transition may refer to any state of the light emitted by the one or more light emitting elements 106 in between a period of peak photopic light and peak scotopic light.

Note that the first and second transitions are merely labels and do not imply an order to the transitions other than that which is explicitly stated.

The first transition occurs over a first transition time period and the second transition occurs over a second, different transition time period. In preferred examples, the second transition time period may be greater than the first transition time period. For example, the second transition time period may be thirty minutes and the first transition time period may be five minutes. Alternatively, the second transition time period may be equal to the first transition time period. In another alternative example, the second transition time period may be less than the first transition time period.

In some examples, the first transition from photopic light to scotopic light and the second transition from photopic light to scotopic light are different only in duration, i.e. only the first and second transition time periods are different.

In preferred examples however, the first transition comprises light of a first intensity profile and the second transition comprises light of a second, different intensity profile, wherein the first intensity profile is different compared to the second intensity profile. The (luminous) intensity profile may characterise the brightness of the light emitted by the one or more light emitting elements 106. The first and second intensity profiles may vary in time and/or space. For example, the second transition may comprise a second intensity profile that is perceived as dusk.

In alternative examples, the first intensity profile is equal to the second intensity profile.

In examples, the first transition from photopic light to scotopic light and the second transition from photopic light to scotopic light are different only in their intensity profile, i.e. only the first and second intensity profiles are different.

In preferred examples, the first transition comprises light of a first spectral profile and the second transition comprises light of a second, different spectral profile. In examples, the first spectral profile is different compared to the second spectral profile. The spectral profile may characterise the colour of the light emitted by the one or more light emitting elements 106. For example, the first transition may comprise light of a first portion of the (visible) electromagnetic spectrum whilst the second transition may comprise light of a second portion of the (visible) electromagnetic spectrum. The first and second spectral profiles may vary in time and/or space.

In examples, the first transition from photopic light to scotopic light and the second transition from photopic light to scotopic light are different only in their spectral profile, i.e. the first and second spectral profiles are different.

In alternative examples, the first transition from photopic light to scotopic light and the second transition from photopic light to scotopic light may be different in any combination of duration, spectral profile and intensity profile. E.g. duration and spectral profile, duration and intensity profile, spectral profile and intensity profile, or duration, spectral profile and intensity profile.

In examples, subsequent to emitting the second period of scotopic light, photopic light is emitted by the one or more light emitting elements 106 for a third time period 305. In examples, the third time period is equal to the first and/or second time period of photopic light. In other examples, the third time period is not equal to the first and/or third time period of photopic light.

In examples, a third transition from scotopic light to photopic light between the first period 302 of scotopic light and the second time period 303 of photopic light is different compared to a fourth transition from scotopic light to photopic light between the second period 304 of scotopic light and the first 301 or third 305 time period of photopic light.

The third transition occurs over a third transition time period and the fourth transition occurs over a fourth transition time period. In preferred examples, the fourth transition time period may be greater than the third transition time period. For example, the fourth transition time period may be thirty minutes and the third transition time period may be five minutes. Alternatively, the fourth transition time period may be equal to the third transition time period. In another alternative example, the fourth transition time period may be less than the third transition time period. In examples, the first and third transition time periods may be equal. In further examples, the second and fourth transition time periods may be equal. In alternative examples, neither the first, second, third nor fourth transition time periods are equal.

In some examples, the third transition from scotopic light to photopic light and the fourth transition from scotopic light to photopic light are different only in duration, i.e. only the first and second transition time periods are different.

In preferred examples however, the third transition comprises light of a third intensity profile and the fourth transition comprises light of a fourth intensity profile, wherein the third intensity profile is different compared to the fourth intensity profile. The third and fourth intensity profiles may vary in time and/or space. In examples, the first and third intensity profiles may be equal. In further examples, the second and fourth intensity profiles may be equal. In alternative examples, neither the first, second, third nor fourth intensity profiles are equal. In further alternative examples, the third intensity profile is equal to the fourth intensity profile.

In examples, the third transition from scotopic light to photopic light and the fourth transition from scotopic light to photopic light are different only in their intensity profile, i.e. only the third and fourth intensity profiles are different.

In preferred examples, the third transition comprises light of a third spectral profile and the fourth transition comprises light of a fourth spectral profile. In examples, the third spectral profile is different compared to the fourth spectral profile. The third and fourth spectral profiles may vary in time and/or space. In examples, the first and third spectral profiles may be equal. In further examples, the second and fourth spectral profiles may be equal. In alternative examples, neither the first, second, third nor fourth spectral profiles are equal. In further alternative examples, the third spectral profile is equal to the fourth spectral profile.

In examples, the third transition from scotopic light to photopic light and the fourth transition from scotopic light to photopic light are different only in their spectral profile, i.e. the third and fourth spectral profiles are different.

In alternative examples, the third transition from scotopic light to photopic light and the fourth transition from scotopic light to photopic light may be different in any combination of duration, spectral profile and intensity profile. E.g. duration and spectral profile, duration and intensity profile, spectral profile and intensity profile, or duration, spectral profile and intensity profile.

In preferred examples, the one or more light emitting elements 106 may emit a repeated light cycle comprising consecutive periods of photopic and scotopic light. An example light cycle is shown in FIG. 3a. The repeated light cycle comprises at least the first and second periods 301-304 of photopic and scotopic light (i.e. the first 301 and second 303 periods of photopic light and the first 302 and second 304 periods of scotopic light).

In examples, the light cycle may additionally comprise the third period of photopic light 305.

In preferred examples, the first and second periods of photopic and scotopic light are contiguous. That is, they are "back-to-back" such that the first period of scotopic light immediately follows the first period of photopic light, the second period of photopic light immediately follows the first period of scotopic light and so on.

In some examples, the third period of photopic light is contiguous with the second period of scotopic light.

In alternative examples, the light emitting elements 106 do not emit a repeated light cycle. In further examples, the light cycle does not repeat. That is, a single light cycle may be emitted.

In examples, the scotopic light 304 emitted for the second time period (the subjective night) is emitted once per light cycle. In these examples, the second transition from photopic light to scotopic light occurs only once per light cycle.

In examples wherein the light cycle comprises the third period of photopic light 305, the fourth transition from scotopic light to photopic light may only occur once per light cycle.

In preferred examples, the light cycle is one day. The light cycle may be exactly or approximately twenty four hours. In alternative examples, the light cycle may be greater than or less than one day. For example, the light cycle may repeat twice every twenty four hours. In another example, the light cycle may be between twenty and twenty eight hours.

For example, the light cycle in FIG. 3b comprises twenty four hours of consecutive periods of photopic and scotopic light consisting of four hours of photopic light (4P), followed by three hours of scotopic light (3S), followed by two hours of photopic light (2P) and two hours of scotopic light (2S), three hours or photopic light (3P), one hour of scotopic light (1S), five hours of photopic light (5P) and four hours of scotopic light (4S). The light cycle then repeats. In this example, 4S is the second period of scotopic light, referred to as the subjective night 304 in FIG. 3b. In other examples, the repeating cycle may be more or less than twenty four hours (e.g. twenty five hours, twenty two hours, twelve hours or forty eight hours). In examples, the periods of photopic and scotopic light may have the same duration. For example, the light cycle may consist of 2P, 2S, 2P, 2S, 2P, 2S, 6P and 6S.

Figure 4:
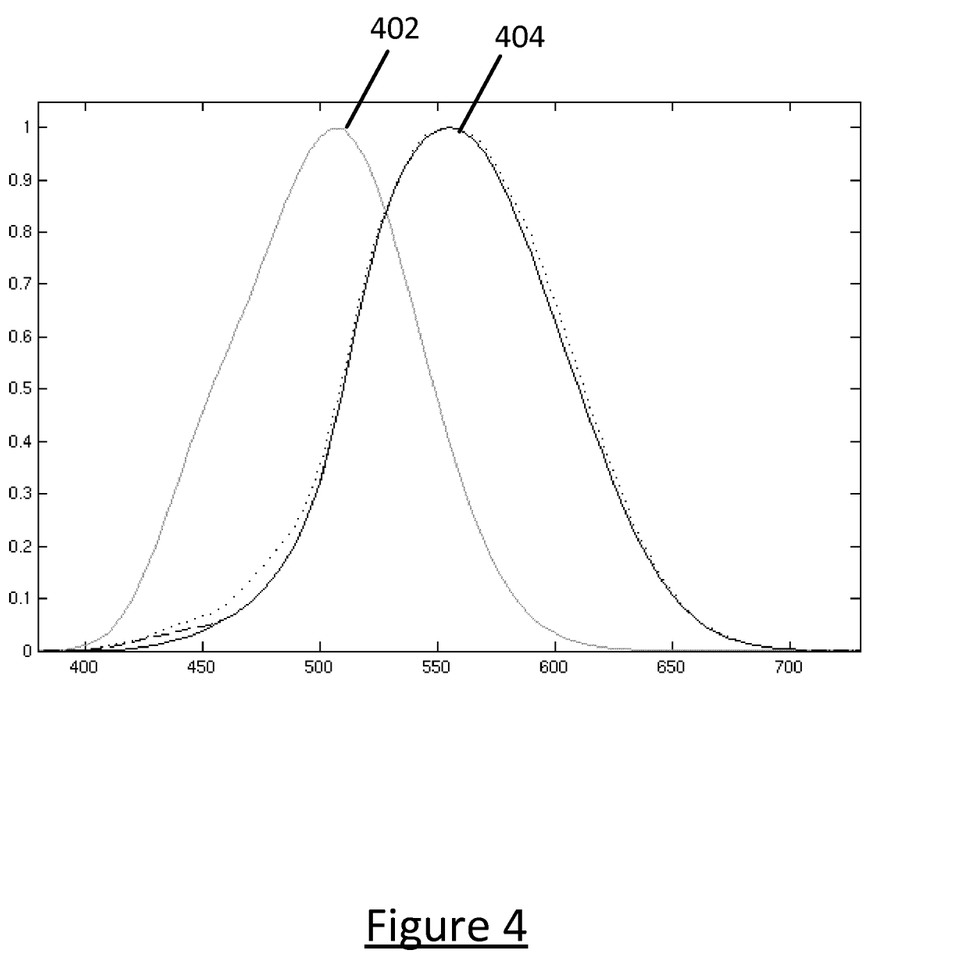
FIG. 4 shows an example photopic and scotopic luminosity functions.

FIG. 4 shows example scotopic (grey) 402 and photopic (black) 404 luminosity functions. The photopic function 404 includes the CIE 1931 standard (solid), the Judd-Vos 1978 modified data (dashed), and the Sharpe, Stockman, Jagla & Jägle 2005 data (dotted).

In examples, the time periods may be programmable by an end-user 102. For example, the end-user 102 may use the lighting control device 108 to program one or more of the time periods. In examples, the transition periods may be programmable by the end-user 102. In examples, the characteristics of the light emitted during periods of photopic light 301 and 303, scotopic light 302 and 304 and/or transition periods may be programmable by the end-user 102. For example, the end-user may 102 set a desired brightness, colour, light scene etc.

In alternatives, the end-user 102 may not be able to change the time periods or light characteristics from the initial settings.

In examples, the photopic light and scotopic light respectively correspond to average human photopic vision and scotopic vision ranges. For example, luminance level (luminous intensity) of the photopic light may be between approximately 1 to $10^8$ cd/m$^2$ and the luminance level of the scotopic light may be between approximately $10^{-6}$ to $10^{-3.5}$ cd/m$^2$.

In alternative examples, the photopic light and scotopic light respectively correspond to average chicken photopic vision and scotopic vision ranges.

In further alternative examples, the photopic light and scotopic light may be programmed by the end-user 102 to correspond to a specific animal's photopic and scotopic vision.

In examples, the end-user 102 may set the light emitted by the one or more light emitting elements 106 (e.g. using the lighting control device 108) to emit photopic and scotopic light corresponding to at least one of: human vision and chicken vision.

The methods described above can be applied to photopic light and scotopic light of any brightness level within the range of photopic and scotopic light that respectively results in photopic and scotopic vision.

In examples, the one or more light emitting elements 106 may be a single type of light emitting diode (LED) or multiple types of LEDs. In examples, the LEDs may be phosphor converted LEDs or direct LEDs and may emit light in the range of ultraviolet to infrared. It will be appreciated that the light emitting elements 106 may be emitting elements other than LEDs.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of emitting light from one or more light emitting elements each controllable to emit respective light, the method comprising:
    emitting a first time period of photopic light,
    followed by emitting a first time period of scotopic light,
    followed by emitting a second time period of photopic light, and
    followed by emitting a second time period of scotopic light;
    wherein a first transition from the first time period of photopic light to the first time period of scotopic light is different compared to a second transition from the second time period of photopic light to the second time period of scotopic light, and/or wherein a third transition from the first time period of scotopic light to the second time period of photopic light is different compared to a fourth transition from the second time period of scotopic light to the first time period of photopic light or to a third time period of photopic light, and
    wherein the photopic light and the scotopic light result in photopic vision and scotopic vision respectively.

2. The method according to claim 1, wherein the first transition occurs over a first transition time period and the second transition occurs over a second, different transition time period and/or the third transition occurs over a third transition time period and the fourth transition occurs over a fourth, different transition time period.

3. The method according to claim 2, wherein the second transition time period is greater than the first transition time period and/or the fourth transition time period is greater than the third transition time period.

4. The method according to claim 1, wherein the first transition comprises light of a first intensity profile and the second transition comprises light of a second, different intensity profile.

5. The method according to claim 1, wherein the first transition comprises light of a first spectral profile and the second transition comprises light of a second, different spectral profile.

6. The method according to claim 1 comprising:
    repeating a light cycle, wherein the repeated light cycle comprises consecutive periods of photopic and scotopic light comprising at least the first and second time periods of photopic light and the first and second time periods of scotopic light.

7. The method according to claim 6, wherein the second time period of scotopic light is emitted once per light cycle.

8. The method according to claim 6, wherein the light cycle is emitted over a time period of one day.

9. The method according to claim 1, wherein the second time period of scotopic light is greater than the first time period of scotopic light and/or the first and second time periods of photopic light.

10. The method according to claim 1, wherein the time periods are programmable by an end-user.

11. The method according to claim 1, wherein the photopic light and scotopic light respectively result in human photopic vision and scotopic vision and provide an illuminance above 30 lx and an illumination below a few lux, respectively.

12. The method according to claim 1, wherein the photopic light and scotopic light respectively result in chicken photopic vision and scotopic vision.

13. The method according to claim 1, wherein the light emitted from the one or more light emitting devices is optical light.

14. A computer program product comprising code embodied on a non-transitory computer-readable storage medium and configured to cause at least one processor to perform the method of claim 1 by controlling the one or more light emitting elements when the at least one processor executes the code.

15. The method of claim 1, wherein one of the first transition and the second transition lasts at least six times longer than the other of the first transition and the second transition, and wherein one of the third transition and the fourth transition lasts at least six times longer than the other of the third transition and the fourth transition.

16. A lighting system comprising one or more light emitting elements each controllable to emit respective light and configured to:
    emit a first time period of photopic light,
    followed by emitting a first time period of scotopic light,
    followed by emitting a second time period of photopic light, and followed by emitting a second time period of scotopic light;
    wherein a first transition from the first time period of photopic light to the first time period of scotopic light is different compared to a second transition from the second time period of photopic light to the second time period of scotopic light, and/or wherein a third transition from the first time period of scotopic light to the second time period of photopic light is different compared to a fourth transition from the second time period of scotopic light to the first time period of photopic light or a third time period of photopic light; and
    wherein the photopic light and the scotopic light result in photopic vision and scotopic vision respectively.

17. The system of claim 16, wherein one of the first transition and the second transition lasts at least six times longer than the other of the first transition and the second transition, and wherein one of the third transition and the fourth transition lasts at least six times longer than the other of the third transition and the fourth transition.

\* \* \* \* \*